United States Patent [19]
Russo

[11] Patent Number: 4,769,014
[45] Date of Patent: Sep. 6, 1988

[54] GASTROENTERIC FEEDING TUBE FOR ENDOSCOPIC PLACEMENT

[75] Inventor: Ronald D. Russo, Barrington, R.I.

[73] Assignee: Superior Biosystems Inc., Cumberland, R.I.

[21] Appl. No.: 57,431

[22] Filed: Jun. 2, 1987

[51] Int. Cl.⁴ ............................................. A61M 25/00
[52] U.S. Cl. ....................................... 604/270; 604/95
[58] Field of Search ........................ 604/270, 280–282, 604/95; 128/656–658

[56] References Cited

U.S. PATENT DOCUMENTS 1,207,479  12/1916  Bisgaad ................................. 604/95
4,516,970   5/1985  Kaufman et al. ..................... 604/270
4,654,036   3/1987  Tolkoff ................................. 604/270

Primary Examiner—Stephen C. Pellegrino
Attorney, Agent, or Firm—Salter & Michaelson

[57] ABSTRACT

A gastroenteric feeding tube for endoscopic placement includes an elongated tubular main portion, a weighted bolus portion on the distal end of the main portion and a flexible cord element which extends from a substantially axial position at the terminal end of the bolus portion. The cord element can be effectively grasped with a forcep of an endoscopic device to enable the feeding tube to be endoscopically placed in a proper location in a patient for use in administering feeding formula to the patient.

10 Claims, 2 Drawing Sheets

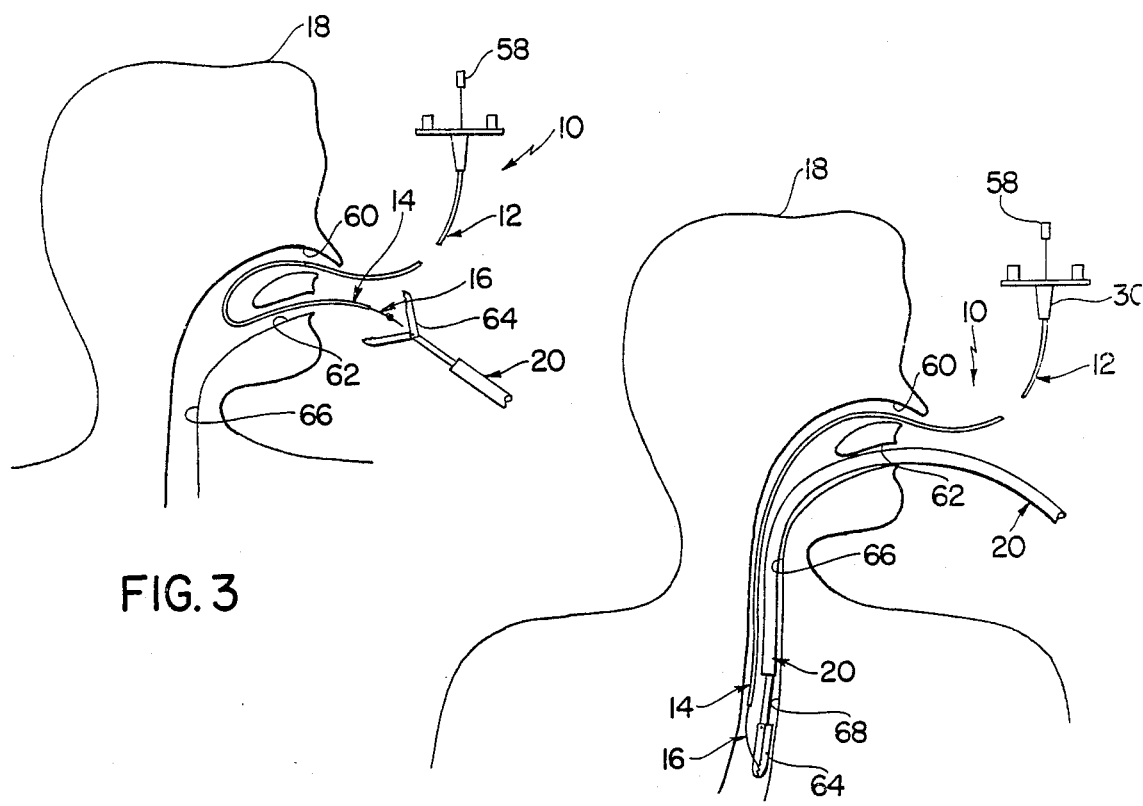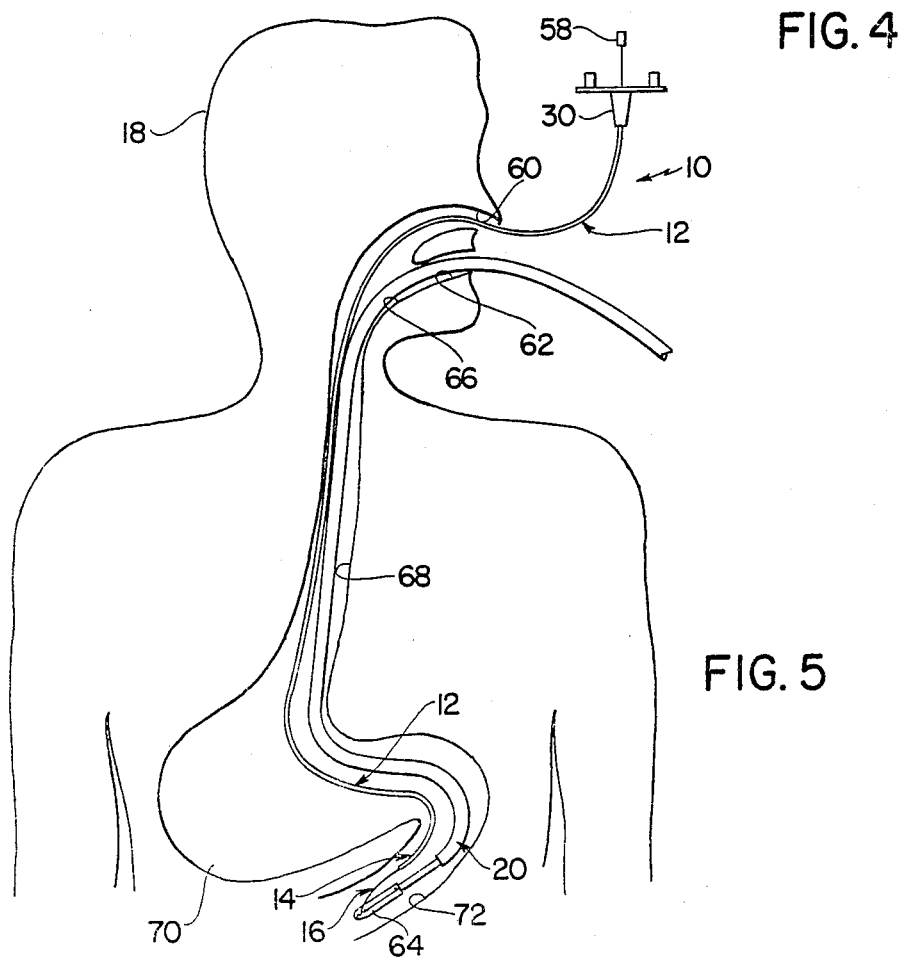

GASTROENTERIC FEEDING TUBE FOR ENDOSCOPIC PLACEMENT

BACKGROUND AND SUMMARY OF THE INVENTION

The instant invention relates to medical apparatus and more particularly to a gastroenteric feeding tube which is adapted for endoscopic placement.

Gastroenteric feeding tubes (sometimes called nasoenteric feeding tubes) have generally been found to be useful for administering feeding formulas to patients who, for various reasons, are unable to meet their normal nutritional requirements through oral intake but who nevertheless have functional gastrointestinal tracts. Generally, a gastroenteric feeding tube comprises an elongated tubular flexible main portion having distal and proximal ends and having at least one side aperture therein adjacent the distal end, and a weighted bolus on the distal end. A feeding tube of this type is generally installed in a patient so that it extends through one of the patient's nostrils, through the esophagus, into the stomach and preferably into the duodenum area of the intestines. Once a gastroenteric feeding tube has been properly installed in a patient in this manner, feeding formula can be effectively administered to the patient by passing it through the tubular main portion so that the formula passes outwardly into the patient's stomach or intestines through the aperture adjacent the distal end of the main portion. Further, once a feeding tube has been installed in a patient in this manner, the weighted bolus is utilized for maintaining the feeding tube in a properly installed position in the patient so that the distal end portion of the feeding tube is not refluxed up into the esophagus during regurgitation. In this connection, for safety reasons, it has generally been found to be essential to prevent the distal end portion of a feeding tube from passing upwardly into a patient's esophagus, since once it is in the esophagus, there is a risk that it will inadvertently pass into the patient's lungs. Further, once the distal end portion of a feeding tube passes into a patient's lungs, there is an even greater risk that feeding formula will be inadvertently introduced into the lungs, causing severe respiratory problems or even death.

It has been found that when prolonged artificial feeding is required, it is generally preferable to install a feeding tube in a patient so that the distal end portion thereof is positioned past the patient's pyloric valve in either the duodenum or the jejunum area of the patient's intestines. In this regard, it has generally been found that more nutritious feeding can be carried out when feeding formula is passed directly into a patient's intestines rather than into the patient's stomach. Further, it has been found that when a feeding tube is installed so that the distal end portion thereof is positioned past a patient's pyloric valve, the tendency of the distal end portion of the feeding tube to be refluxed up into the patient's esophagus during regurgitation is significantly reduced.

One technique which has heretofore been found to be effective for installing a feeding tube in a patient is to utilize a wire stylet which is inserted into the main lumen of the tube to add stiffness thereto so that it can be manipulated during installation procedures. However, while this technique has generally proven to be an effective method for installing a feeding tube so that the bolus portion thereof is positioned in the stomach of a patient, it has not been found to be effective for moving the bolus portion of a feeding tube past the pyloric valve of a patient and into the duodenum or jejunum area of the patient's intestines. Accordingly, heretofore it has generally been the practice to first install a feeding tube in a patient so that the bolus portion thereof is located in the patient's stomach and to then rely on the patient's own peristaltic action to move the bolus portion past the pyloric valve of the patient. However, it has often been found that when a patient requires the use of a gastroenteric feeding tube, the patient is also suffering from a loss of mobility due to illness or medication. Hence, in many cases a patient may also be suffering from impaired or loss of peristaltic action so that the patient is incapable of passing the bolus end portion of a feeding tube past his or her pyloric valve without assistance.

Recently, it has been found that endoscopic procedures can be utilized for installing gastroenteric feeding tubes in patients so that the bolus portions thereof are positioned beyond the pyloric valves of patients. In this regard, a number of relatively sophisticated fiberoptic endoscopic devices have recently been developed which can be effectively utilized for mechanically moving the distal end portions of feeding tubes past the pyloric valves of patients. More specifically, endoscopic devices have been developed which are operable with appliances having grasping or snaring forceps on the distal ends thereof which can be utilized for grasping the ends of feeding tubes to install them in patients. Unfortunately, however, it has been found that most of these endoscopic devices are extremely delicate, and that they cannot be utilized for effectively manipulating feeding tubes having any significant degrees of stiffness. On the other hand, although feeding tubes must generally be soft enough to enable them to be comfortably installed in patients, they must also have sufficient degrees of stiffness to retain them in patients and to prevent them from being inadvertently withdrawn as the endoscopic devices which are utilized for installing them in patients are removed. Accordingly, it has been found that it can often be very difficult to install conventional gastroenteric feeding tubes in patients utilizing endoscopic procedures.

While heretofore several attempts have been made to adapt feeding tubes for endoscopic placement, these attempts have generally been found to be unsuccessful. Specifically, attempts have been made to adapt feeding tubes by passing sutures through the walls of the distal end portions thereof so that the sutures can be grasped by endoscopic devices for more effectively manipulating the feeding tubes as they are installed in patients. However, it has been found that when sutures are passed through the walls of feeding tubes in this manner, they can generally easily tear out during installation procedures. Further, it has been found that when sutures are passed through the walls of the bolus portions of the feeding tubes, they produce openings therein so that the weighted elements in the bolus portions are exposed to stomach fluids. Further, it has been found that sutures which extend through the sidewalls of feeding tubes are generally less than effective, since they inherently extend from the sides of the tubes rather than the ends thereof, and as a result they cannot be utilized for axially guiding or advancing the feeding tubes to install them in patients. Other attempts have been made to adapt feeding tubes for endoscopic placement by securing rings on the distal ends thereof. However, it has been found that rings also pull out of the distal end portions of feeding tubes and that it can be difficult to disengage the forceps of endoscopic devices from rings or the like.

The instant invention provides a gastroenteric feeding tube which is effectively adapted for endoscopic placement. More specifically, the instant invention provides a gastroenteric feeding tube comprising an elongated tubular flexible main portion having a longitudinally extending lumen therein, the main portion having distal and proximal ends and having at least one side aperture therein adjacent the distal end, a weighted bolus extending in substantially aligned relation from the distal end of the main portion and terminating in a terminal end, and a flexible cord element attached to the bolus so that it extends in substantially aligned relation from the terminal end. The bolus is preferably integrally formed with the main portion of the feeding tube, and it preferably has substantially the same cross-sectional dimension and configuration as the main portion. The bolus preferably comprises a tubular wall portion which extends from the distal end of the main portion, means sealing the interior of the wall portion of the bolus from the lumen in the main portion, weighting means contained in the wall portion and an end cap for sealing the terminal end of the wall portion of the bolus. The end cap preferably has an axial bore therethrough, and the cord element preferably extends in sealed relation through the axial bore, and it includes an enlarged first end which is disposed on the inner side of the end cap to retain the cord element from passing through the bore. Further, the end cap preferably has an A Durometer Scale hardness of greater than 110 to prevent the cord element from tearing out of the end cap, and the main portion and the bolus portion of the feeding tube preferably have an A Durometer Scale hardness of between 80 and 100 to enable the feeding tube to be comfortably installed and retained in a patient.

It has been found that the feeding tube of the instant invention can be effectively installed in a patient using endoscopic procedures. Specifically, because the feeding tube of the subject invention includes a flexible cord element which extends axially from the terminal end of the feeding tube, it can be easily manipulated utilizing an endoscopic device to install the bolus portion of the feeding tube in a position past the pyloric valve of the patient. In this regard, the flexible cord element provides a buffer between an endoscopic device and the bolus portion of a feeding tube which enables the feeding tube to be easily manipulated despite the inherent stiffness thereof. Further, since the cord element extends from the axis of the terminal end of the tube, the feeding tube can be effectively axially advanced so that it can be accurately placed and guided through the stomach and past the pyloric valve of a patient. Still further, because the bolus and main portions of the feeding tube are of substantially the same diameter, there is generally sufficient clearance in the esophagus and pyloric valve areas of a patient to easily accommodate both the bolus and an endoscopic device. Still further, because of the relative hardness of the end cap portion of the feeding tube, the cord element is not easily torn from the bolus portion.

Accordingly, it is a primary object of the instant invention to provide an effective feeding tube for endoscopic placement.

Another object of the instant invention is to provide a gastroenteric feeding tube which can be effectively manipulated with an endoscopic forcep to enable it to be installed in a patient with the bolus portion of the feeding tube positioned past the patient's pyloric valve.

A still further object of the instant invention is to provide an effective feeding tube for endoscopic placement which includes a cord element which extends from an axial position at the terminal end of the bolus portion of the feeding tube.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIGS. 3 through 5 are sequential views illustrating the installation of the feeding tube in a patient.

DESCRIPTION OF THE INVENTION

Figures 1, 2:
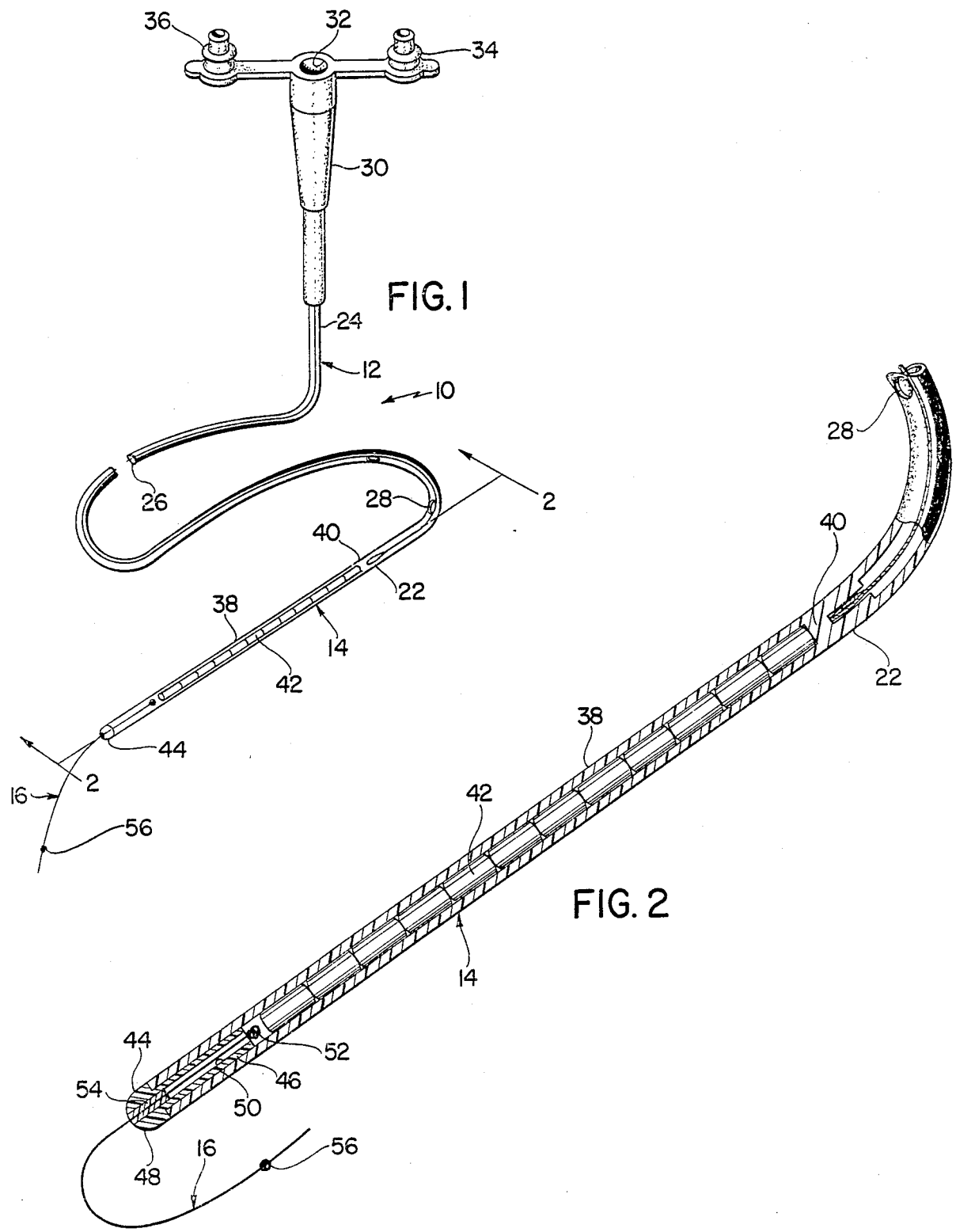
FIG. 1 is a perspective view of the feeding tube of the instant invention.
FIG. 2 is an enlarged fragmentary sectional view of the bolus and cord element of the feeding tube.

Referring now to the drawings, the feeding tube of the instant invention is illustrated in FIGS. 1 through 5 and generally indicated at 10 in FIGS. 1 and 3 through 5. The feeding tube 10 comprises an elongated tubular flexible main portion generally indicated at 12, a weighted bolus portion generally indicated at 14 on an end of the main portion 12, and a flexible cord element generally indicated at 16 on the terminal end of the bolus portion 14. The feeding tube 10 is adapted to be installed in a patient 18 utilizing an endoscopic device of the type generally indicated at 20 in FIGS. 3 through 5 so that the bolus portion 14 and the cord element 16 are positioned in the intestinal area of the patient 18 as will hereinafter be more fully set forth.

The main portion 12 is of elongated tubular configuration, and it has a distal end 22 and a proximal end 24. A main lumen 26 extends axially through the main portion 12, and a plurality of side apertures 28 are formed in the main portion 12 adjacent the distal end 22, the apertures 28 extending between the main lumen 26 and the exterior of the main portion 12. The main portion 12 is preferably made from a polyether-based polyurethane, and it preferably has an A Durometer Scale hardness of between 80 and 100 and most preferably of approximately 90. The main portion 12 is preferably formed in a 12 French size so that it has an outside diameter of approximately 0.160 inch and an inside diameter of approximately 0.115 inch.

An adapter 30 is provided on the proximal end 24 of the main portion 12 for connecting the feeding tube 10 to a source of feeding formula. In this regard, the adapter 30 is formed with an axial passage 32 therein, and it includes a closure plug 34 and an adapter plug 36, which are alternatively receivable in the passage 32 for closing the end thereof or for adapting it for receiving tubular fittings of smaller diameter, as is well known in the art.

The bolus portion 14 extends integrally from the distal end 22 of the main portion 12, and it includes a sidewall portion 38, a first seal 40, a plurality of weighting elements 42, and a second seal or tip portion 44. The wall portion 38 is preferably made from a polyether-based polyurethane, and it preferably extends integrally from the tubular main portion 12, terminating in a terminal end. The wall portion 38 preferably also has a substantially circular cross section, and it preferably has substantially the same interior and exterior diameters as the tubular main portion 12. The seal 40 is positioned adjacent the distal end 22 of the main portion 12, and it is operative for sealing the interior of the bolus portion 14 from the main lumen 26. The seal 40 is preferably made from a urethane-based material so that it effectively bonds to the interior of the tubular main portion 38 to seal the interior of the bolus portion 14 from the lumen 26. The weighting elements 42 are preferably made from a suitable corrosion-resistant non-toxic metal such as stainless steel in order to minimize injury to the patient 18 in the event of a rupture in the wall portion 38. The weighting elements 42 are preferably of cylindrical configuration, and they preferably have lengths of approximately ¼ inch to provide an adequate degree of flexibility in the bolus portion 14. Further, the bolus portion 14 preferably includes a sufficient quantity of the weighting elements 42 to provide a weight of at least 3 grams and preferably a weight of approximately 8 grams in the bolus portion 14. The tip portion 44 is preferably formed so that it includes a reduced cylindrical insert portion 46 and a rounded tip portion 48. The insert portion 46 is preferably formed so that it is receivable in the interior of the wall portion 38 adjacent the terminal end thereof, and the tip portion 44 is integrally attached to the insert portion 46 and preferably formed so that it provides a rounded terminal end on the bolus portion 14. An axial bore 50 having a diameter which is only slightly greater than that of the cord element 16 is formed in the tip portion 44 for receiving the cord element 16 therethrough in order to secure the latter to the bolus portion 14. The tip portion 44 is preferably also made from a suitable polyurethane, such as a polyether-based polyurethane, and it is preferably permanently secured to the wall portion 38 with a suitable urethane-based adhesive. The tip portion 44 preferably has an A Durometer Scale hardness of greater than 100 and, in fact, preferably greater than 110 in order to prevent the cord element 16 from being pulled out of the end of the bolus portion 14 when the cord element is assembled therewith in a manner hereinafter more fully set forth. In this regard, it has been found that when the tip portion 44 is constructed in the manner herein set forth, it can generally prevent the cord element 16 from being pulled out by the forces which are normally applied by endoscopes during installation procedures, i.e., forces of less than approximately 5 pounds.

The cord element 16 preferably comprises a suitable flexible cord, and it is preferably made from a suitable inert multifilament string material. In this regard, it has been found that conventional silk suture material can be effectively utilized for the cord element 16 since silk suture material is generally highly supple and inert, although the use of other materials for the cord element 16 is contemplated. The cord element 16 is preferably formed with an enlarged upper end 52 which is herein embodied as a double knot, and the cord element 16 preferably has an overall length of at least approximately 2 inches. The cord element 16 is assembled with the tip portion 44 so that it extends through the axial bore 50 therein and so that the enlarged end 52 is positioned adjacent the inner end of the tip portion 44 to prevent the cord element 16 from being pulled through the bore 50. A seal 54 made from a suitable sealing material, such as a urethane-based adhesive, is provided in the interior of the bore 52 for sealing the cord element 16 to the interior of the bore 50 and for thereby sealing the terminal end of the bolus portion 14. The cord element 16 is preferably assembled and dimensioned so that it extends at least 1 inch beyond the terminal end of the bolus portion 14 and preferably approximately 2 inches therebeyond, and a second enlarged end 56 is formed by a knot in the cord element 16 adjacent the free end thereof.

Referring now to FIGS. 3 through 5, the procedure utilized for endoscopically installing the feeding tube 10 in the patient 18 is illustrated. In this regard, before the feeding tube 10 is installed in the patient 18, a conventional wire stylet 58 is preferably inserted into the feeding tube 10 so that it extends through the lumen 26 to the distal end 22 of the main portion 12 for providing increased rigidity in the main portion 12 during installation of the feeding tube 10. After the stylet 58 has been installed in the feeding tube 10, the cord element 16 and the bolus portion 14 are passed through a nostril 60 and out through the mouth 62 of the patient 18. The cord element 16 is then grasped with a forcep 64 on the terminal end of the endoscope 20, and the terminal end portion of the endoscope 20 is fed back in through the mouth 62 so that the forcep 64, the cord element 16, and the bolus portion 14 pass through the throat 66 and the esophagus 68 and into the stomach 70 of the patient 18. Once the forcep 64, the cord element 16 and the bolus portion 14 have been passed into the stomach 70, they are preferably further advanced past the pyloric valve (not shown) of the patient and into the duodenum area 72. Thereafter the cord element 16 is released from the forcep 64 and the endoscope 20 is withdrawn, leaving the feeding tube 10 in a properly installed position in the patient 18.

The feeding tube 10 has several specific features which make it effectively adapted for endoscopic placement in accordance with the above procedures. Specifically, the cord element 16 extends axially from the terminal end of the bolus portion 14 so that as the feeding tube 10 is installed in the patient 18, the bolus 14 can be accurately guided and advanced in an axial direction utilizing the endoscope 20. In this regard, it is important for the feeding tube 10 to be axially advanced by pulling on the axis of the bolus portion 14 rather than by pulling on the sidewall 38 in order to minimize stress to the patient 18 and also in order to enable the bolus portion 14 to be effectively and accurately manipulated with the relatively delicate forcep 64. Further, the cord element 16 is highly supple and flexible, and, as a result, it operates as a buffer between the forcep 64 and the bolus portion 14 so that the inherent stiffness of the bolus portion 14 and the main portion 10 with the stylet 58 therein is not transmitted directly to the forcep 64 and the endoscope 20. Still further, the overall construction and hardness of the tip portion 44 enable the tip portion 44 to effectively prevent the cord element 16 from being pulled out of the bolus 14. In this regard, the overall construction of the tip portion 44 enables the tip portion 44 to effectively withstand pulling forces of at least up to 5 pounds in order to prevent the cord element 16 from being pulled out of the bolus 14. Still further, the overall construction of the feeding tube 10 so that the bolus 14 extends integrally from the main portion 12 and has substantially the same exterior diameter as the main portion 12 enables the feeding tube 10 to be effectively accommodated in the body of a patient along with the endoscope 20 during installation procedures. Still further, the overall stiffness of the main portion 12 and the bolus portion 14 enable the feeding tube 10 to be retained in a properly installed position in the patient 18, particularly during removal of the endoscope 20.

It is seen therefore that the instant invention provides a gastroenteric feeding tube which is effectively adapted for endoscopic placement. The overall construction of the main portion 12 and the bolus portion 14 and the manner in which the cord element 16 is secured to the bolus portion 14 provide effective benefits. In particular, these features cooperate to substantially facilitate the endoscopic placement of the feeding tube 10 in a patient, such as the patient 18. They also cooperate to minimize stress to the patient 18 during installation procedures. Accordingly, for these reasons as well as the other reasons hereinabove set forth, it is seen that the feeding tube of the instant invention represents a significant advancement in the art which has substantial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A gastroenteric feeding tube comprising an elongated tubular flexible main portion having a longitudinally extending lumen therein, said main portion having distal and proximal ends and having at least one side aperture therein which extends between said lumen and the exterior of said main portion adjacent said distal end thereof, a weighted bolus portion extending in substantially aligned relation from the distal end of said main portion and having a terminal end and a flexible cord element attached to said bolus portion so that it extends outwardly a distance from substantially the axis of said bolus portion beyond said terminal end terminating in a free end.

2. In the gastroenteric feeding tube of claim 1, said bolus portion and said main portion having substantially the same cross-sectional dimension.

3. In the gastroenteric feeding tube of claim 2, said bolus portion and said main portion both being of substantially circular cross section and being substantially axially aligned.

4. In the gastroenteric feeding tube of claim 1, said cord element further characterized as a multifilament cord element.

5. In the gastroenteric feeding tube of claim 4, said bolus portion extending integrally from said main portion.

6. In the gastroenteric feeding tube of claim 1, said bolus portion comprising a tubular wall portion extending from the distal end of said main portion and terminating in a terminal end, means sealing the interior of said wall portion from said lumen adjacent the distal end of said main portion, weighting means contained in said wall portion and means sealing the terminal end of said wall portion, said cord element extending from said terminal end sealing means.

7. In the gastroenteric feeding tube of claim 6, said terminal end sealing means comprising an end cap, said end cap defining the terminal end of said bolus portion, said cord element extending through said end cap.

8. In the gastroenteric feeding tube of claim 7, said end cap having an axial bore therethrough, said cord element having an enlarged first end and extending through said axial bore with said enlarged first end disposed on the inner side of said end cap to retain said cord element from passing through said bore.

9. In the gastroenteric feeding tube of claim 8, said end cap having an A Durometer Scale hardness of greater than 110.

10. In the gastroenteric feeding tube of claim 9, said main portion and said bolus sidewall portion being integrally formed and having an A Duromeeter Scale hardness of less than 100.

* * * * *

REEXAMINATION CERTIFICATE (1207th)
United States Patent [19]

Russo

[11] B1 4,769,014

[45] Certificate Issued Feb. 13, 1990

[54] GASTROENTERIC FEEDING TUBE FOR FEEDING ENDOSCOPIC PLACEMENT

[75] Inventor: Ronald D. Russo, Barrington, R.I.

[73] Assignee: Superior Biosystems Inc., Cumberland, R.I.

Reexamination Request:
No. 90/001,741, Apr. 3, 1989

Reexamination Certificate for:
Patent No.: 4,769,014
Issued: Sep. 6, 1988
Appl. No.: 57,431
Filed: Jun. 2, 1987

[51] Int. Cl.⁴ .......................... A61M 25/00
[52] U.S. Cl. .......................... 604/270; 604/95
[58] Field of Search .......... 604/270, 280–282, 604/95; 128/656, 658

[56] References Cited

U.S. PATENT DOCUMENTS

| | | | |
|---|---|---|---|
| 1,207,479 | 12/1916 | Bisgaard | 604/95 |
| 3,948,272 | 4/1976 | Guibor | 604/264 |
| 4,516,970 | 5/1985 | Kaufman et al. | 604/270 |
| 4,654,036 | 3/1987 | Tolkoff | 604/270 |

FOREIGN PATENT DOCUMENTS

1139442 9/1981 U.S.S.R.

*Primary Examiner*—Stephen C. Pellegrino

[57] ABSTRACT

A gastroenteric feeding tube for endoscopic placement includes an elongated tubular main portion, a weighted bolus portion on the distal end of the main portion and a flexible cord element which extends from a substantially axial position at the terminal end of the bolus portion. The cord element can be effectively grasped with a forcep of an endoscopic device to enable the feeding tube to be endoscopically placed in a proper location in a patient for use in administering feeding formula to the patient.

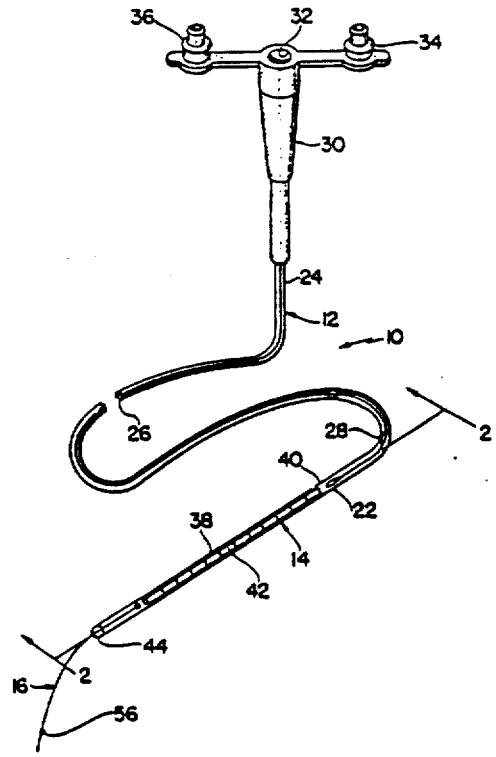

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2-10, dependent on an amended claim, are determined to be patentable.

1. A gastroenteric feeding tube comprising an elongated tubular flexible main portion having a longitudinally extending lumen therein, said main portion having distal and proximal ends and having at least one side aperture therein which extends between said lumen and the exterior of said main portion adjacent said distal end thereof, a weighted bolus portion extending in substantially aligned relation from the distal end of said main portion and having a terminal end and a *highly supple and* flexible cord element attached to said bolus portion so that it extends outwardly a distance from substantially the axis of said bolus portion beyond said terminal end terminating in a free end.

* * * * *